(12) United States Patent
Juskaitis et al.

(10) Patent No.: US 6,507,687 B1
(45) Date of Patent: Jan. 14, 2003

(54) IMAGING APPARATUS

(75) Inventors: Rimvydas Juskaitis, Oxford (GB); Mark Andrew Aquilla Neil, Botley (GB); Tony Wilson, Oxford (GB)

(73) Assignee: ISIS Innovation Limited, Oxfordshire (GB)

( * ) Notice: Subject to any disclaimer, the term of this patent is extended or adjusted under 35 U.S.C. 154(b) by 0 days.

(21) Appl. No.: 09/647,539

(22) PCT Filed: Apr. 9, 1999

(86) PCT No.: PCT/GB99/01088

§ 371 (c)(1),
(2), (4) Date: Nov. 15, 2000

(87) PCT Pub. No.: WO99/52416

PCT Pub. Date: Oct. 21, 1999

(30) Foreign Application Priority Data

Apr. 9, 1998  (GB) .............................................. 9807832

(51) Int. Cl.[7] .................................................. G02B 6/06
(52) U.S. Cl. ...................................................... 385/116
(58) Field of Search ................................. 385/115, 116, 385/117, 119

(56) References Cited

U.S. PATENT DOCUMENTS

| | | | |
|---|---|---|---|
| 4,862,873 A | 9/1989 | Yajima et al. ................. | 128/6 |
| 5,166,787 A | 11/1992 | Irion ............................ | 358/98 |
| 5,586,132 A | * 12/1996 | Levy ........................... | 385/115 |

FOREIGN PATENT DOCUMENTS

| | | |
|---|---|---|
| DE | 3818104 A1 | 12/1988 |
| DE | 19532095 C1 | 8/1996 |
| WO | WO 97/31282 | 8/1997 |

* cited by examiner

*Primary Examiner*—Javaid Nasri
(74) *Attorney, Agent, or Firm*—Drinker Biddle & Reath LLP

(57) ABSTRACT

The confocal imaging apparatus includes first and second light sources (6, 7) located at opposite ends of a fibre optic bundle (1). One end of the fibre optic bundle (4) is located adjacent the object to be imaged the opposite end of the fibre optic bundle (2) is located adjacent a camera (3) that records the images received from the fibre optic bundle (4). An analyser (10) is used to extract a confocal image from the image of the object produced using the illumination from the first light source (6) and the image of the object produced using illumination from the second light source (7). The imaging apparatus is particularly suited to endoscopy applications and is able to provide video rate confocal images.

10 Claims, 4 Drawing Sheets

IMAGING APPARATUS

FIELD OF INVENTION

The present invention relates to imaging apparatus and in particular to apparatus capable of providing optically sectioned images that may be overlaid to form a three dimensional image. The present invention is particularly suited, but not exclusively, to endoscopy applications employing a fiber optic bundle.

BACKGROUND OF THE INVENTION

A conventional fiber optic endoscope consists of a fiber optic bundle that is inserted into a human or animal body to the object to be imaged. The end of the fiber optic bundle outside of the body is usually connected to a camera whereas the opposite end of the fiber optic bundle inside the body has a light source that illuminates the site of interest. Scattered light from the object is imaged onto the end of the fiber optic bundle and is guided along the bundle to the camera. The image received by the camera is a conventional image with no depth information other than that obtainable from a simple lens system. Hence, the conventional endoscope is unable to provide optically sectioned images that might be used to create three dimensional images of the object inside the body. Moreover, the light source is usually located inside the body adjacent the object because difficulties arise with back reflections from the end of the optical fibers when the light is transmitted to the site of interest along the fiber optic bundle from the outside.

SUMMARY OF THE INVENTION

The present invention seeks to provide an imaging system that is arranged to provide optically sectioned images using a bundle of small light conduits such as optical fibers.

The present invention provides imaging apparatus comprising a first light source; a bundle of light conduits along which light from the first light source passes; a second light source; a lens system for focussing light from the bundle of light conduits onto a specimen and for focussing light scattered from the specimen back to the bundle of light conduits; and an analyzer for extracting an optically sectioned image of the specimen from first and second images of the specimen, the first image being of the specimen illuminated by the first light source and the second image being of the specimen illuminated using the second light source.

Preferably, the bundle of light conduits is a fiber optic bundle.

In a first embodiment of the present invention the first light source is positioned at a first end of the fiber optic bundle and the second light source is positioned at the opposite second end of the fiber optic bundle near to the specimen. Ideally, a beam splitter is provided between the end of the fiber optic bundle and the lens system whereby light from the second light source is introduced into the path of light emerging from the fiber optic bundle.

In an alternative embodiment of the present invention the optical fibers of the bundle are encased in a cladding medium and light from the first light source is coupled to the cladding medium. A prism may be provided for coupling light from the first light source with the cladding medium. Alternatively, the cladding medium may include an integral grating for coupling light from the first light source with the cladding medium. With this embodiment the second light source may be located at either the first or the second end of the fiber optic bundle.

Preferably, the first and second light sources provide substantially identical illumination of the specimen.

In an alternative aspect the present invention provides an adapter for a microscope having a light source and lens system including an objective lens, the adapter comprising a bundle of light conduits along which light from the microscope passes and a second light source, the bundle of light conduits and the second light source being positioned between the microscope light source and the objective lens whereby optically sectioned images of a specimen are extracted from first and second images of the specimen, the first image being of the specimen illuminated by the adapter light source and the second image being of the specimen illuminated using the microscope light source.

An embodiment of the present invention will now be described by way of example with reference to the accompanying drawings, in which:

DETAILED DESCRIPTION OF THE DRAWINGS

Figure 1:
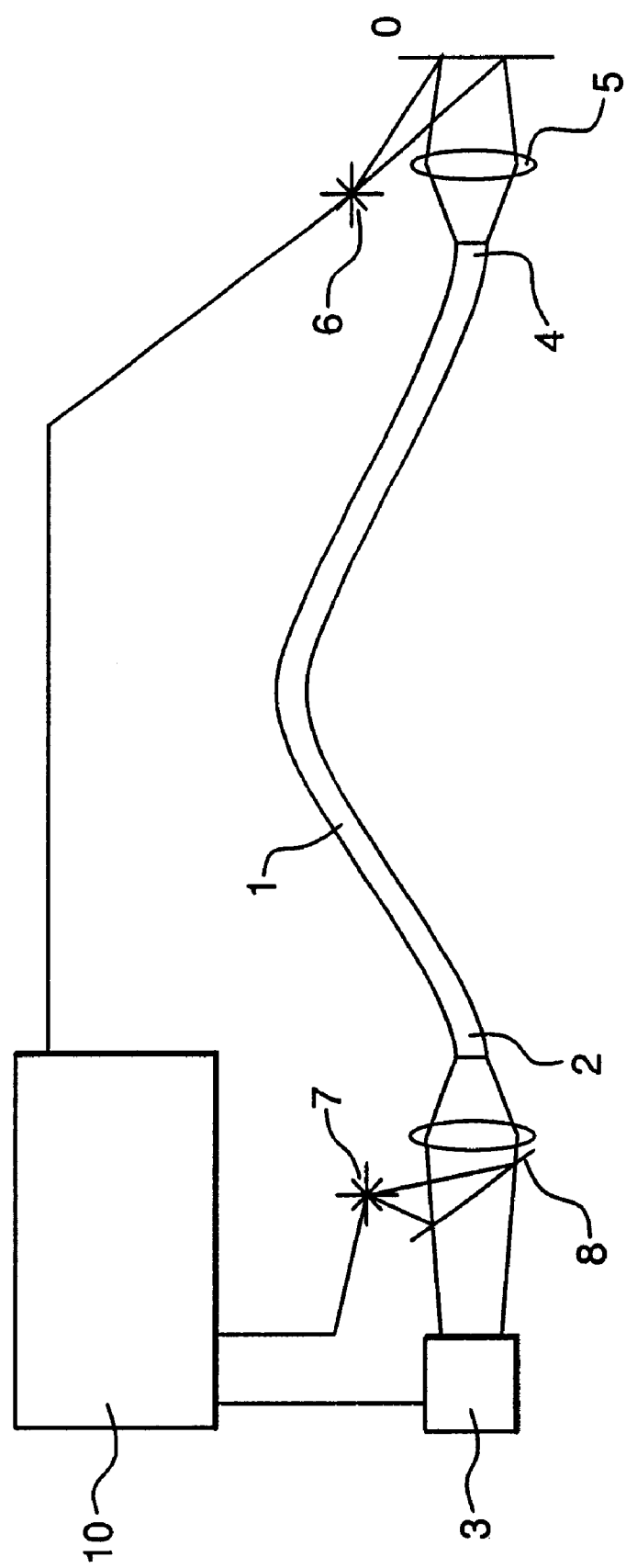
FIG. 1 is a schematic diagram of imaging apparatus in accordance with the present invention.

The imaging apparatus shown in FIG. 1 employs a bundle 1 of optically guiding, high refractive index, cores or light conduits embedded in a lower refractive index cladding matrix surrounded by an outer light absorbing sleeve, such as a bundle of optical fibers. As long as the geometrical arrangement of the light conduits is preserved along the length of the bundle, then images received at one end of the bundle are transmitted faithfully with minimal loss of information to the opposite end of the bundle. Light falling on the cladding matrix between the light conduits is not guided along the bundle and instead the light is attenuated through absorption by the outer sleeve. This attenuation of the light falling on the cladding matrix is used to maintain the contrast of the image received by the camera at the opposite end of the fiber optic bundle.

In FIG. 1 it may be seen that a first end 2 of the fiber optic bundle 1 is aligned with a camera 3 so that images transmitted by the bundle 1 may be recorded. At the opposite, second end 4 of the fire optic bundle a lens system 5 is provided, only one objective lens is shown in FIG. 1, and a light source 6. In addition to the light source 6, a second light source 7 is provided adjacent the first end 2 of the fiber optic bundle. A beam splitter 8 such as a semi-silvered mirror is used to direct the light from the second light source 7 into the first end 2 of the fiber optic bundle 1 whilst still permitting the first end of the fiber optic bundle to be imaged by the camera 3.

Figure 2:
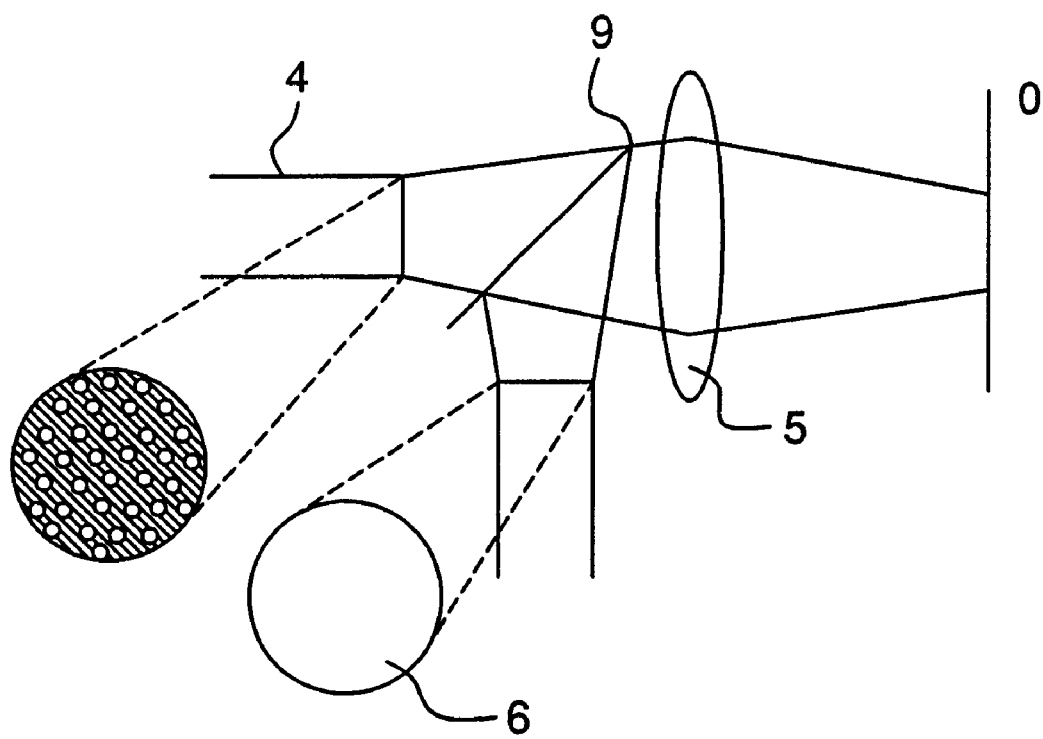
FIG. 2 is a schematic diagram of the illumination system of the imaging apparatus of FIG. 1.

As seen more clearly in FIG. 2, a second beam splitter 9 such as a semi-silvered mirror is provided between the second end 4 of the fiber optic bundle and the objective lens 5. The second beam splitter 9 ensures that the light from the first and second light sources 6, 7 follow similar paths through the objective lens to the site of interest and back to the second end of the fiber optic bundle 1.

The two light sources 6, 7 and the camera 3 are connected to a controller 10 that controls operation of the light sources and analyses the images recorded by the camera.

With the imaging apparatus described above, images including optically sectioned properties are produced from which the optically sectioned image can be extracted. When the fiber optic bundle is illuminated by the second light source and is focused (i.e. resolved) onto the object O by the objective lens 5, light scattered by the object O is imaged exactly back into the optical fibers at the second end 4 producing a bright image at the first end 2. On the other hand, when the object is out of focus, then the scattered light is imaged substantially equally into the optical fibers and the cladding matrix. This in turn produces a dimmer image because the light in the cladding is absorbed by the sleeve. For a three dimensional object, parts of the object will be exactly in focus whereas other parts will not be in focus and that portion of the object which is in focus will appear as a much brighter image at the first end 2 of the fiber optic bundle. In this way the image produced at the first end 2 of the fiber optic bundle is a composite image consisting of a conventional image (i.e. non-sectioning) in combination with a sectioned image.

This composite image $I_1$ that is received by the camera 3 is then analyzed by the controller 10 to extract the sectioned image $I_s$ from the composite image. To extract the sectioned image a purely conventional image 12 is also required which is subtracted from the composite image $I_1$ leaving the sectioned image $I_s$ remaining. The conventional image is obtained by first illuminating the object O using only the first light source 6 and recording the image produced before re-illuminating the object using only the second light source 7 to produce the composite image.

To ensure reliable extraction of the sectioned image, it is important that the illumination provided by the first light source 6 is substantially the same as the illumination provided by the second light source 7. The illumination provided by both light sources should be uniform across the field of view and should not have the core structure of the bundle present in the light incident on the object. It is for this reason that the arrangement of FIG. 2 is preferred. Corrections for small differences in the intensities of the illumination patterns can be accommodated by employing normalization factors $N_1$ and $N_2$ and computing $N_2I_2-N_1I_1$.

By recording two images, one conventional image and one composite image, at different focal positions a three dimensional image of the object can be created, The changes in focal position can be achieved by moving the objective lens position or by employing a vari-focal lens system. As only two images are required for each focal position because the entire image is produced instantaneously, video rate imaging is easily achieved and scanning across the object is avoided.

Figure 3:
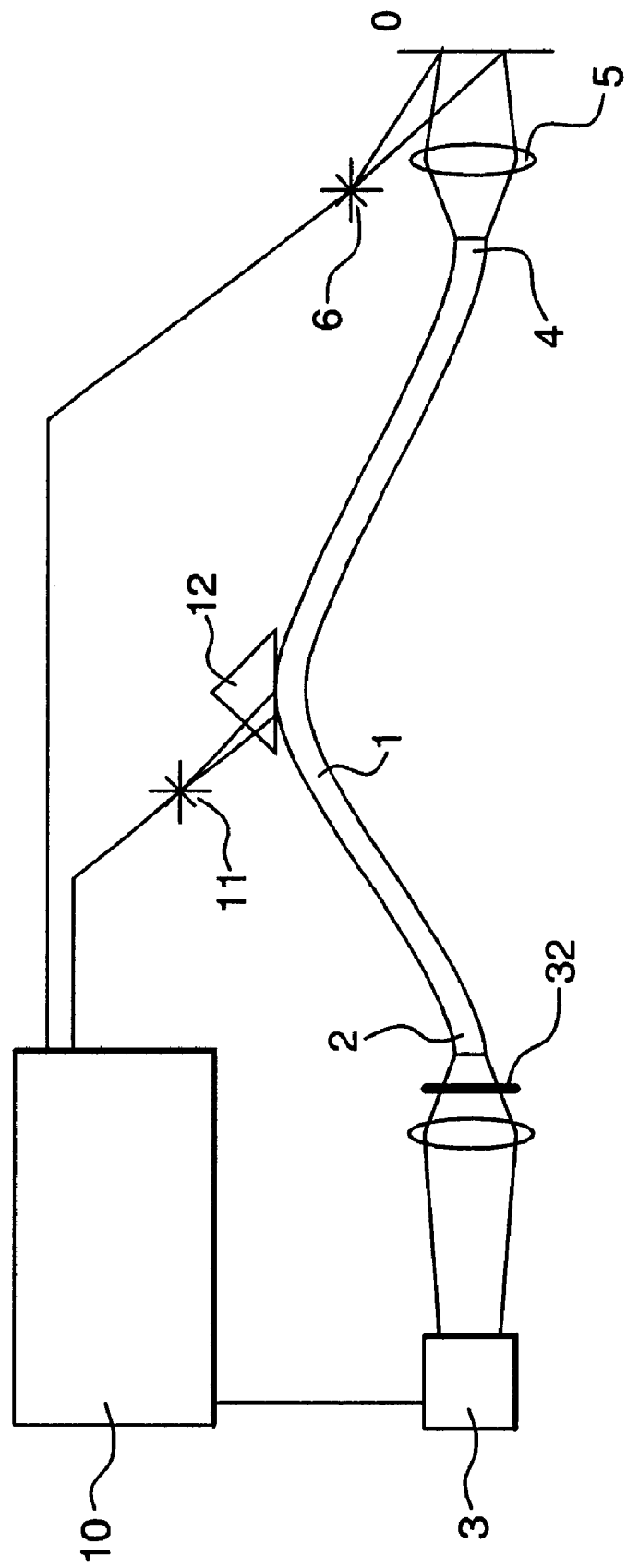
FIG. 3 is a schematic diagram of alternative imaging apparatus in accordance with the present invention.

Particularly in endoscopy applications, the presence of the first light source 6 adjacent the object may be undesirable as it increases the complexity and size at the end of the fiber optics bundle inserted into the body Alternative imaging apparatus is shown in FIG. 3. The second light source 7 is omitted and an alternative third light source 11 is provided coupled to the cladding of the fiber optics bundle As shown in FIG. 3 the light source may be coupled to the cladding using a prism 12. Alternative means of coupling the light source 11 to the cladding by destroying the internal reflections of the cladding are also envisaged such as a grating. With this arrangement the outer light absorbing sleeve is removed from the bundle between the coupling point and the second end 4 of the fiber optic bundle to avoid attenuation of the light in the cladding and to enable the light coupled to the cladding to travel along the bundle to the object O.

With this alternative apparatus the light coupled to the cladding is not injected into the optical fibers and instead forms an inverse image of that produced by the light source 6. For an object exactly in focus, light from the cladding is focused onto the object in the same way as before and the light scattered from the object is focused back into the cladding. This light is then absorbed in the length of the fiber optic bundle between the coupling point and the first end 2 of the bundle where the absorbing sleeve remains present. Alternatively, a suitable mask 32 may be introduced at the first end so as to block any light propagating towards the camera from the cladding region whilst permitting light from the core regions of the bundle to pass. This produces a dark image at the first end 2 that is recorded by the camera 8. When the object is out of focus, some of the light from the cladding will be scattered by the object and directed into the optical fibers which produces a brighter image for the camera at the first end 2 of the bundle. Thus, when the third light source 11 is used on its own a composite image $I_3$ is produced of a conventional image minus a sectioned image. As before the sectioned image ran be extracted by computing $I_2-I_3$ (or $N_2I_2-N_3I_3$ where necessary). This imaging apparatus provides the additional advantage that the sectioned image is twice as bright as that produced by the apparatus of FIGS. 1 and 2.

A further alternative imaging apparatus employs the second and third light sources 7 and 11 only. This arrangement has the advantage that the problems of light reflected from the faces of the fiber optic bundle, which occur when the first light source 6 is used, do not arise.

Figure 4:
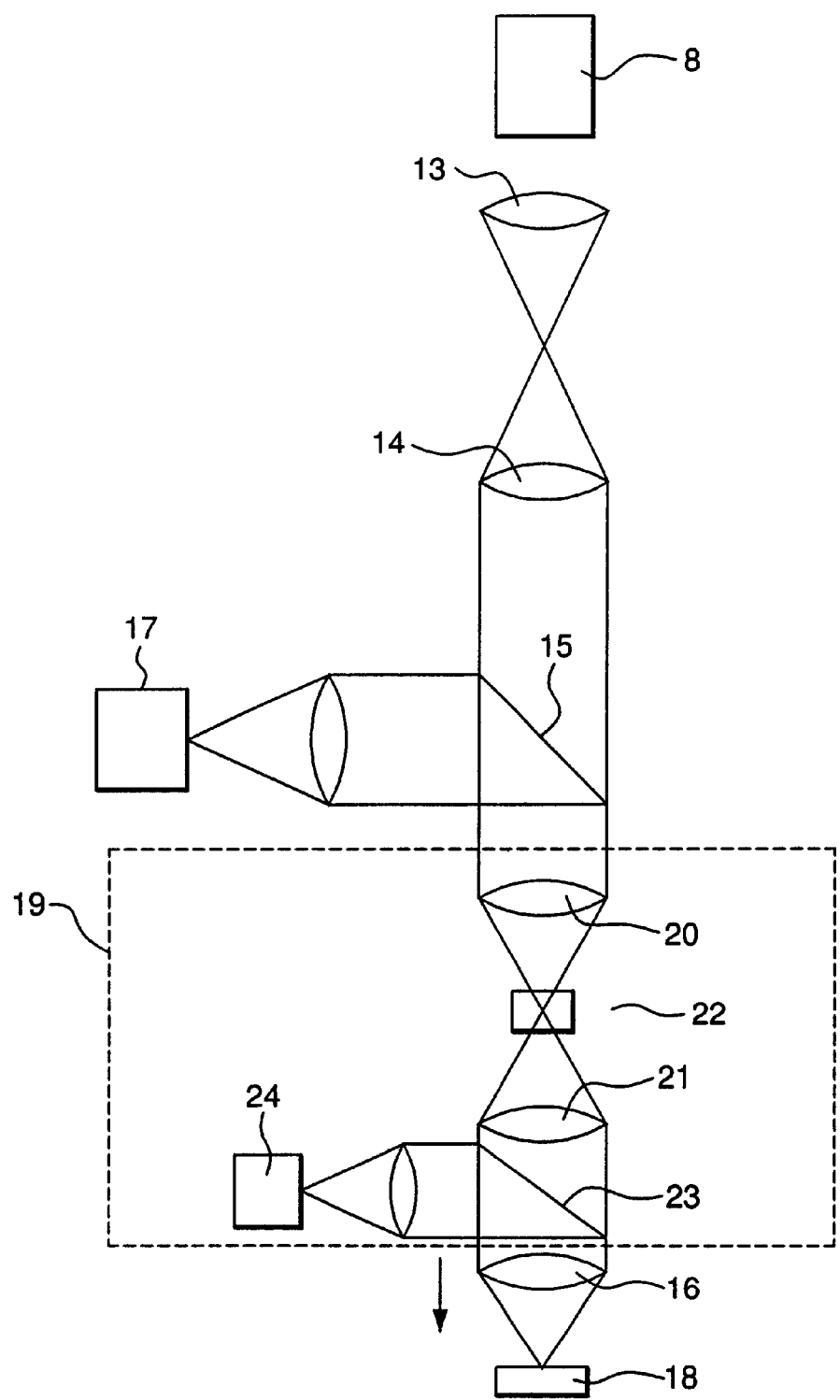
FIG. 4 is a schematic diagram of conversion apparatus for use with a conventional microscope.

Whilst the above description has focused on endoscopy applications both medial and non-medical, for example internal inspection of machines, the imaging apparatus may be used in a wide variety of applications employing conventional microscopes. FIG. 4 shows how a conventional microscope may be adapted to incorporate this imaging apparatus. The microscope includes an eye piece 13, a tube lens 14, a beam splitter 15, an objective lens 16 and a light source 17. The microscope usually operates in reflective mode with the specimen 18 located beyond the objective lens 16. In order to adapt the microscope to produce optically sectioned images (i.e. a confocal microscope) an optical sectioning adapter 19 is added between the beam splitter 15 and the objective lens 16. The optical sectioning adapter 19 consists of two lens systems 20, 21 which are positioned either end of a fiber optic bundle 22 or other bundle of small cross-section light conduits. Beyond the second of the two lens systems 21 a beam splitter 23 is provided in combination with a second light source 24. As with the imaging apparatus described with reference to FIGS. 1, 2 and 3, in passing through the fiber optic bundle the light from the first light source 17 acquires structure in cross-section for the bundle this enables a sectioned image to be formed for those portions of the object that are in focus in combination with a conventional image of those portions of the object that are out of focus. The light from the second light source 24 does not pass through the fiber optic bundle and so generates a purely conventional image. The subtraction of the two images provides an optically sectioned image of the object that can be built up to form a three dimensional image by adjustment of the conventional lenses 14, 16.

The imaging apparatus is particular suited to endoscopy applications, however, the range of applications is much greater than this and indeed the imaging apparatus may be employed in almost all circumstances where an optically sectioned image is required. The advantages of the imaging system are that no moving parts are required to produce an optically sectioned image. Also, non-laser as well as laser light sources can be used, for example for fluorescent imaging or a light emitting diode.

What is claimed is:

1. Imaging apparatus for generating an optically sectioned image of a specimen, the imaging apparatus comprising:

a first light source;

a second light source;

a fiber optic bundle having a first end and a second end and arranged such that scattered first source light that has been scattered from said specimen when illuminated by the first light source and scattered second source light that has been scattered from said specimen when illuminated by the second light source is collected at the second end and is guided to the first end;

a lens system for focusing light from the second end of the fiber optic bundle onto said specimen and for focusing light scattered from said specimen to the second end of the fiber optic bundle; and an analyzer for receiving light from the first end of the fiber optic bundle scattered first source light and scattered second source light and for extracting an optically sectioned image of said specimen from both the scattered first source light and the scattered second source light wherein the fiber optic bundle is adapted to apply structure to light from the first light source that is guided by the fiber optic bundle to said specimen and wherein the second light source and the fiber optic bundle are arranged such that either the fiber optic bundle applies a structure to light from the second light source incident on said specimen which is different to the structure applied by the fiber optic bundle to light from the first light source or the fiber optic bundle applies no structure to light from the second light source incident on said specimen.

2. Imaging apparatus as claimed in claim 1, wherein the first light source is positioned at the first end of the fiber optic bundle and the second light source is positioned beyond the second end of the fiber optic bundle near to the specimen.

3. Imaging apparatus as claimed in claim 2, wherein a beam splitter is provided between the second end of the fiber optic bundle and the lens system whereby light from the second light source is introduced into a path parallel to light emerging from the second end of the fiber optic bundle.

4. Imaging apparatus as claimed in claim 1, wherein the fiber optic bundle comprises a plurality of light conduits encased in a cladding medium and light from the second light source is coupled to the cladding medium.

5. Imaging apparatus as claimed in claim 4, wherein a prism is provided for coupling light from the second light source to the cladding medium.

6. Imaging apparatus as claimed in claim 4, wherein a mask is provided at the first end of the fiber optic bundle for absorbing light propagating through the cladding medium.

7. Imaging apparatus as claimed in claim 4, wherein the second light source is located at the first end of the fiber optic bundle.

8. Imaging apparatus as claimed in claim 1, wherein the first and second light sources are lasers.

9. Imaging apparatus as claimed in claim 1, wherein the first and second light sources provide substantially identical illumination of the specimen.

10. Imaging apparatus as claimed in claim 1, wherein a focal position of the lens system is adjustable and the analyzer is adapted to produce a three dimensional image of the specimen from a plurality of sets of first and second images, each set at a different focal position.

* * * * *